US00PP30273P3

(12) United States Plant Patent
Klemm et al.

(10) Patent No.: US PP30,273 P3
(45) Date of Patent: Mar. 5, 2019

(54) ***DIANTHUS* PLANT NAMED 'KLEDP16232'**

(50) Latin Name: *Dianthus caryophyllus*
Varietal Denomination: KLEDP16232

(71) Applicant: Klemm+Sohn GmbH & Co. KG, Stuttgart (DE)

(72) Inventors: Nils Klemm, Stuttgart (DE); Lena Gutbrodt, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/731,290

(22) Filed: May 18, 2017

(65) Prior Publication Data

US 2018/0338402 P1 Nov. 22, 2018

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./273
See application file for complete search history.

*Primary Examiner* — Keith O. Robinson
(74) *Attorney, Agent, or Firm* — Bethany R. Roahrig; Cochran Freund & Young LLC

(57) ABSTRACT

A new *Dianthus* plant particularly distinguished by large, red-purple flowers, and an upright habit, is disclosed.

1 Drawing Sheet

Genus and species: *Dianthus caryophyllus*.
Variety denomination: 'KLEDP16232'.

BACKGROUND OF THE NEW PLANT

The present invention comprises a new and distinct variety of *Dianthus*, botanically known as *Dianthus caryophyllus*, and hereinafter referred to by the variety name 'KLEDP16232'. 'KLEDP16232' originated from a controlled cross between the proprietary female parent 'DCP-2009-1001' (unpatented) and the proprietary male parent 'DCP-2009-0187' (unpatented) in May 2011 in Stuttgart, Germany. A single plant was selected in June 2012 and designated 'KLEDP16232'.

In August 2012, 'KLEDP16232' was first vegetatively propagated by vegetative cuttings. 'KLEDP16232' was found to reproduce true to type in successive generations of asexual propagation in Stuttgart, Germany via vegetative stem cuttings.

SUMMARY

The following are the most outstanding and distinguishing characteristics of this new variety when grown under normal horticultural practices in Stuttgart, Germany.

1. Red-Purple flowers;
2. Large flowers; and
3. An upright habit.

DESCRIPTION OF THE PHOTOGRAPH

This new *Dianthus* plant is illustrated by the accompanying photograph of a plant approximately 8 weeks old and grown in a greenhouse in Stuttgart, Germany. The photograph shows the whole plant, including the flowers and foliage and buds and was taken in April 2016 in Stuttgart, Germany.

The colors shown are as true as can be reasonably obtained by conventional photographic procedures.

DESCRIPTION OF THE NEW VARIETY

The following detailed descriptions set forth the distinctive characteristics of 'KLEDP16232'. The data which define these characteristics were collected from asexual reproductions carried out in Stuttgart, Germany. Data was collected in April 2017 on 7-month old plants grown in a plastic greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus*.
- *Common*.—Pot carnation.
- *Designation*.—'KLEDP16232'.

Parentage:
- *Female parent*.—The proprietary *Dianthus* variety 'DCP-2009-1001' (unpatented).
- *Male parent*.—The proprietary *Dianthus* variety 'DCP-2009-0187' (unpatented).

Plant:
- *Plant form*.—Upright, potted plant.
- *Plant height*.—13.0 cm to 15.0 cm.
- *Plant diameter or spread*.—18.0 cm to 22.0 cm.
- *Propagation type*.—Vegetative cuttings, stem cutting.
- *Time to produce a rooted young plant*.—14 to 16 days.
- *Root description*.—White, RHS NN155B, fine.
- *Rooting habit* (*shape*).—Lanceolate.

Lateral branches:
- *Length*.—12.0 cm to 14.0 cm.
- *Diameter*.—0.3 cm to 0.5 cm.
- *Number of lateral branches with flower buds or flowers of the second order*.—5.

*Flower clustering on lateral branches.*—In some lateral branches.
*Internode length.*—2.5 cm to 4.0 cm.
*Number of internodes per branch/stem.*—4 to 6.
*Node length.*—0.2 cm to 0.4 cm.
*Node diameter.*—0.4 cm to 0.6 cm.
*Thickness of the internode of the stem.*—Thin.
*Texture.*—Smooth.
*Color.*—RHS 133A.
*Branch/stem appearance.*—Solid.

Foliage:
*Arrangement.*—Opposite.
*Length.*—6.0 cm to 8.0 cm.
*Width.*—0.6 cm to 0.8 cm.
*Shape.*—Lanceolate.
*Apex.*—Acute.
*Base.*—Obtuse.
*Margin.*—Entire.
*Texture (both upper and lower surfaces).*—Smooth.
*Glaucosity of the leaf.*—Medium.
*Curvature of the leaf.*—Moderately recurved.
*Immature leaf color.*—Upper surface: RHS 144A. Lower surface: RHS 144A.
*Mature leaf color.*—Upper surface: RHS 137A. Lower surface: RHS 137B.
*Venation pattern.*—Palmate.
*Venation color.*—Upper surface: RHS 137A. Lower surface: RHS 137B.

Flowers:
*Flower type and habit.*—Round, double, small sprays.
*Fragrance.*—Present, sweet.
*Natural flowering season.*—Spring to fall.
*Position of flowers relative to the foliage.*—Slightly above.
*Number of flowers per spray.*—3 to 4.
*Flower longevity on the plant.*—10 to 14 days.
*Buds.*—Length: Approximately 2.0 cm. Diameter: 1.0 cm to 1.2 cm. Shape: Elliptic. Color: RHS 139B and RHS 144A. Extrusion of the styles at the bud stage: Absent.
*Corolla.*—Quantity of petals and arrangement: 18 to 20. Corolla height: 1.5 cm to 2.0 cm. Corolla diameter: 2.7 cm. Petal length: 3.0 cm. Petal width: 1.5 cm to 2.0 cm. Petal shape: Spoon-shaped. Petal apex: Obtuse. Petal base: Acute. Petal margin: Crenate. Depth of petal margin: Medium. Petal texture (both upper and lower surfaces): Smooth. Petal color: Immature: Upper surface: RHS 72A. Lower surface: RHS N78A. Mature: Upper surface: RHS 72B. Lower surface: RHS 77B.
*Calyx.*—Quantity of sepals and arrangement: Composed of 5 sepals. Shape: Campanulate. Logitudinal axis of lobes: Convex. Apex: Acute. Length of calyx lobe: 1.8 cm. Calyx height: 2.0 cm to 2.4 cm. Calyx diameter (at the apex): 0.8 cm to 1.0 cm. Sepal texture (both upper and lower surfaces): Smooth. Sepal color: Upper surface: RHS 137A. Lower surface: RHS 137D.

Peduncles:
*Length.*—12.0 cm.
*Diameter.*—0.2 cm.
*Strength.*—Moderate.
*Texture.*—Smooth.
*Color.*—RHS 133A.

Reproductive organs:
*Stamens.*—Quantity per flower: 7 to 10. Filament length: 0.6 cm to 0.8 cm. Filament color: RHS 157B. Anther length: 0.1 cm. Anther diameter: 0.05 cm. Anther color: RHS 161A. Pollen amount: Absent.
*Pistils.*—Quantity per flower: 1. Pistil length: 0.1 cm. Style length: 0.4 cm to 0.6 cm. Style color: RHS 155B. Shoulder of style: Absent. Number of styles: 4. Stigma shape: Filamentous. Stigma color: RHS N74C. Ovary size: 0.8 cm to 1.0 cm. Ovary shape: Oval. Ovary surface: Smooth. Ovary color: RHS 144A and RHS 145A.

Fruit and seed set: Seed is sometimes observed, but no information on the seed is available.

Disease and pest/insect resistance: No disease and pest/insect resistance observed.

COMPARISON WITH PARENTAL LINE AND KNOWN VARIETY

'KLEDP16232' is distinguished from its parents as described in Table 1.

TABLE 1

Comparison with Parental Lines

| Characteristic | 'KLEDP16232' | Female Parent 'DCP-2009-1001' | Male Parent 'DCP-2009-0187' |
|---|---|---|---|
| Flower color | Red-Purple | Cherry red | Yellow |

'KLEDP16232' can be compared to the commercial *Dianthus* variety Roselly Violet (unpatented). Differences between the varieties are described in Table 2.

TABLE 2

Comparison with Similar Variety

| Characteristic | 'KLEDP16232' | Roselly Violet |
|---|---|---|
| Flower size | Larger than Roselly Violet | Smaller than 'KLEDP16232' |
| Style performance | Absent at bud stage | Present at bud stage |

We claim:

1. A new and distinct variety of *Dianthus* plant designated 'KLEDP16232' as illustrated and described herein.

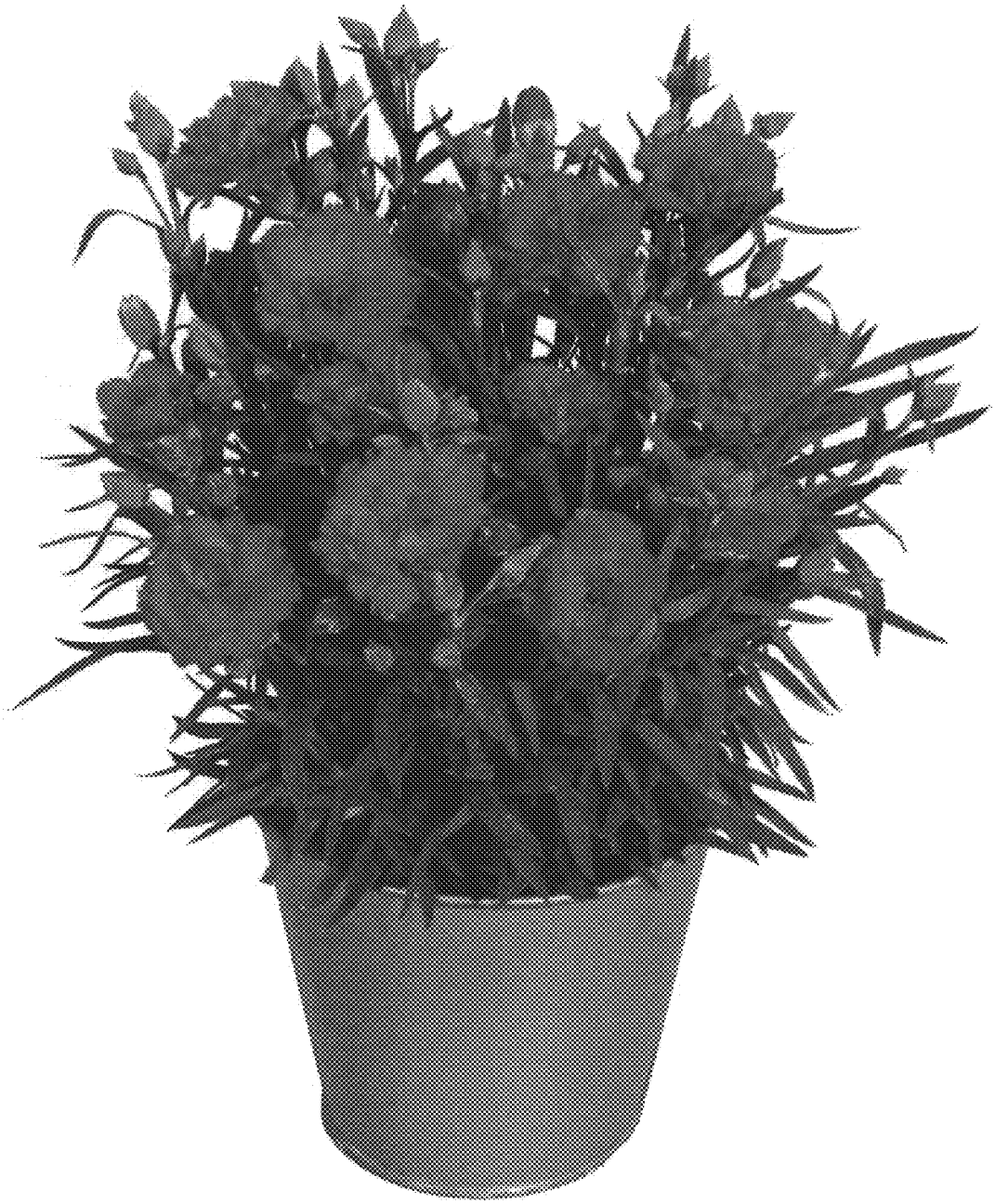

* * * * *